United States Patent [19]

Palmour

[11] Patent Number: 4,875,083
[45] Date of Patent: Oct. 17, 1989

[54] METAL-INSULATOR-SEMICONDUCTOR CAPACITOR FORMED ON SILICON CARBIDE

[75] Inventor: John W. Palmour, Raleigh, N.C.

[73] Assignee: North Carolina State University, Raleigh, N.C.

[21] Appl. No.: 113,572

[22] Filed: Oct. 26, 1987

[51] Int. Cl.$^4$ .................... H01L 29/24; H01L 29/93; H01L 29/94

[52] U.S. Cl. .................. 357/23.6; 357/14; 357/61

[58] Field of Search ............ 357/23.6, 14, 51, 61

[56] References Cited

U.S. PATENT DOCUMENTS

| | | | |
|---|---|---|---|
| 2,918,396 | 12/1959 | Hall | 357/61 |
| 2,981,877 | 4/1961 | Noya | 357/68 |
| 3,201,666 | 8/1965 | Hall | 357/61 |
| 3,254,280 | 5/1966 | Wallace | 357/16 |
| 3,402,332 | 9/1968 | Thire | 357/23.6 |
| 3,497,773 | 2/1970 | Kisinko et al. | 357/51 |

FOREIGN PATENT DOCUMENTS 57-88758  6/1982  Japan .................. 357/14

OTHER PUBLICATIONS

Silicon Carbide Field-Effect and Bipolar Transistors: Muench et al.; pp. 337-339, IEEE IEDM, Tech. Digest, Dec. 1977.
Schottky-Barrier Field-Effect Transistors of 3C-SiC; S. Yoshida et al.; Appl. Phys., vol. 60, No. 8, 10-15-86, pp. 2989-2991.
β-SiC MESFET's and Buried-Gate JFET's; Kelner et al.; IEEE Electron. Device Lett. EDL-8, #9, 1987, p. 428.
Temperature Dependence of the Current-Voltage Characteristics of Metal-Semiconductor Field-Effect Transistors in n—Type B-SiC Grown Via Chemical Vapor Deposition;
Kong et al.; Appl. Phys. Lett., vol. 51, No. 6, 8-10-87, pp. 442-444.
Bearse, Microwaves, vol. 15, No. 5, pp. 9 and 13, May, 1976.
Harris, Solid State Electronics, vol. 19, pp. 103-105, 1976.
Hamilton and Howard, Basic IC Engineering, McGraw-Hill, NT, 1925, pp. 13-16.

Primary Examiner—William D. Larkins
Attorney, Agent, or Firm—Bell, Seltzer, Park & Gibson

[57] ABSTRACT

The invention comprises a metal-oxide-semiconductor (MOS) capacitor formed on silicon carbide. By utilizing new techniques for obtaining single crystals and monocrystalline thin films of silicon carbide, and by positioning the ohmic contact and the metal contact on a common side of the silicon carbide semiconductor portion, devices are obtained which are commercially viable and which demonstrate reduced series resistance, lesser leakage current and greater capacitance than have previous devices formed on silicon carbide.

14 Claims, 2 Drawing Sheets

METAL-INSULATOR-SEMICONDUCTOR CAPACITOR FORMED ON SILICON CARBIDE

FIELD OF THE INVENTION

The present invention relates to a metal-insulator-semiconductor capacitor, and in particular relates to a metal-oxide-semiconductor capacitor formed on silicon carbide.

BACKGROUND OF THE INVENTION

Silicon carbide has been a perennial candidate for use in semiconductor devices. Silicon carbide has long been recognized as having particular characteristics which give it excellent potential for producing semiconductor devices having superior characteristics to devices formed of other commonly used semiconductor materials such as silicon (Si), gallium arsenide (GaAs), and indium phosphide (InP). Silicon carbide has a wide bandgap, a high melting point, a low dielectric constant, a high breakdown field strength, a high thermal conductivity and a high saturated electron drift velocity. These characteristics give devices made from silicon carbide the potential to operate at higher temperatures, in closer proximity to one another, at higher power levels, and a number of other circumstances under which devices made from other semiconductor materials simply could not perform.

In spite of these known characteristics, commercial quality devices formed of silicon carbide have not been forthcoming. Silicon carbide is an extremely difficult material to work with which crystallizes in well over 150 different polytypes. Accordingly, forming the large single crystals of a single polytype or the thin films of particular polytypes of silicon carbide which are required to produce electronic devices on semiconductor materials has remained an elusive goal.

Recently, however, a number of developments have been accomplished in this field which have made the production of commercial quality electronic devices on silicon carbide possible for the first time. These developments are the subject of co-pending patent applications assigned to the common assignee of the present invention and include the following applications which are incorporated herein by reference:

Davis et al, "Growth of Beta-SiC Thin Films and Semiconductor Devices Fabricated Thereon," Ser. No. 07/113,921 filed Oct. 26, 1987; Davis et al.; "Homoepitaxial Growth of Alpha-SiC Thin Films and Semiconductor Devices Fabricated Thereon," Ser. No. 07/113,573, filed Oct. 26, 1987; Davis et al. "Sublimation of Silicon Carbide to Produce Large, Device Quality Single Crystals of Silicon Carbide," Ser. No. 07/113,565, filed Oct. 26, 1987; and Edmond et al "Implantation and Electrical Activation of Dopants into Monocrystalline Silicon Carbide," Ser. No. 07/113,561, filed Oct. 26, 1987, now abandoned.

As discussed in these applications, it is now possible to grow thin films of both alpha (6H hexagonal) and beta (3C cubic) thin films of silicon carbide where such thin films are required, and to appropriately grow large single crystals of silicon carbide where these are required.

One type of electronic device useful in a number of applications is the capacitor. One type of capacitor is known as a metal-insulator-semiconductor capacitor (MIS capacitor). Because silicon is the most commonly used semiconductor material and silicon dioxide is the most commonly used insulator material used in conjunction with silicon, these devices are most commonly referred to as metal-oxide-semiconductor capacitors (MOS capacitors). The term MOS capacitor will be used throughout this application, but it will be understood that the discussions are appropriately applied to MIS capacitors as well.

MOS capacitors can be used, for example, as temperature sensors, by monitoring the shift in threshold or flatband voltage of the capacitor with changes in temperature. Additionally, at a given temperature, a MOS capacitor can be used as a gas sensor by monitoring the shift in the threshold or flatband voltage as a function of the partial pressure of the gas. Additionally, as stated earlier, MOS capacitors could be used as capacitors in various circuit designs, particularly in conjunction with other devices formed from silicon carbide.

Several researchers have described attempts to produce MOS capacitors on silicon carbide. Suzuki et al., *Thermal Oxidation of SiC and Electrical Properties of Al-SiO$_2$-SiC MOS Structure*, Jap. J. Appl. Phys., Vol. 21, No. 4, p. 579, 1982, discuss MOS structures having an aluminum, silicon dioxide and silicon carbide structure, but in which ohmic contacts were made to the back side of the semiconductor substrate, i.e. the side opposite the metal-semiconductor contact. This particular positioning of the contact leads to a certain amount of series resistance in the device which in turn limits its capacitance range. Such series resistance is not typically a problem for MOS capacitors formed on silicon. Silicon carbide, however, is a much more resistive material, and exhibits decreased capacitance in MOS capacitors formed according to Suzuki's design.

Shibahara et al., *Metal-Oxide-Semiconductor Characteristics of Chemical Vapor Deposited Cubic-SiC*, Jap. J. Appl. Phys., Vol. 23, No. 11, 1984, p. L-862, also discuss an aluminum and silicon dioxide MOS capacitor on a 3C silicon carbide thin film. Shibahara, however, made the ohmic contact on the back of a 10 micrometer thin film of silicon carbide after a silicon substrate had been etched off. Such a device design would be far too thin and difficult to handle for any practical commercial applications.

Two other researchers, Fung et al., *Thermal Oxidation of 3C Silicon Carbide Single Crystal Layers on Silicon*, Appl. Phys. Lett., 45(7), Oct. 1984, p. 757; and Avila et al., *Behavior of Inversion Layers in 3C Silicon Carbide*, Appl. Phys. Lett., 49(6), Aug. 1986, p. 334, also studied MOS structures with double-column mercury probes. These discussions are characterization techniques, however, and do not represent viable device designs.

Accordingly, there exists no suitable device design for producing commercial quality MOS capacitors on silicon carbide.

Therefore, it is an object of the present invention to provide a metal-insulator-semiconductor capacitor with reduced series resistance and lesser leakage current, suitable for operation at high temperatures and high radiation densities. The capacitor comprises a semiconductor portion, an active portion of insulated material upon the semiconductor portion, a metal portion upon the insulator portion for defining the active region, and an ohmic contact upon the semiconductor portion and positioned in close proximity to both the active portion of the insulator and the active region of the semiconductor.

It is another object of the invention to provide an MOS capacitor wherein the semiconductor portion is formed of monocrystalline silicon carbide.

It is a further object of the invention to provide an MOS capacitor wherein the ohmic contact on the semiconductor portion is positioned in direct contact with the insulator portion.

SUMMARY OF THE INVENTION

The invention is a metal-oxide-semiconductor (MOS) capacitor that utilizes silicon carbide as the semiconductor material. In preferred embodiments, the capacitor utilizes a circular metal contact on top of an oxide layer on SiC. This design, by placing a large area ohmic contact in close proximity to the silicon carbide region being depleted under the metal oxide contact, greatly reduces series resistance in the device, which in turn increases the capacitance range.

The foregoing objects and advantages and other features of the invention will be more appropriately understood from the detailed description, taken in conjunction with the accompanying drawings in which:

DETAILED DESCRIPTION

The invention is a metal-oxide-semiconductor (MOS) capacitor that utilizes silicon carbide (SiC) as a semiconductor material. The invention can be formed upon an appropriate silicon carbide crystal of any polytype. The use of silicon carbide, which as discussed earlier is a wide bandgap semiconductor, allows the MOS capacitor of the present invention to operate at much higher temperatures than MOS capacitors formed from silicon or gallium arsenide.

Figure 1:
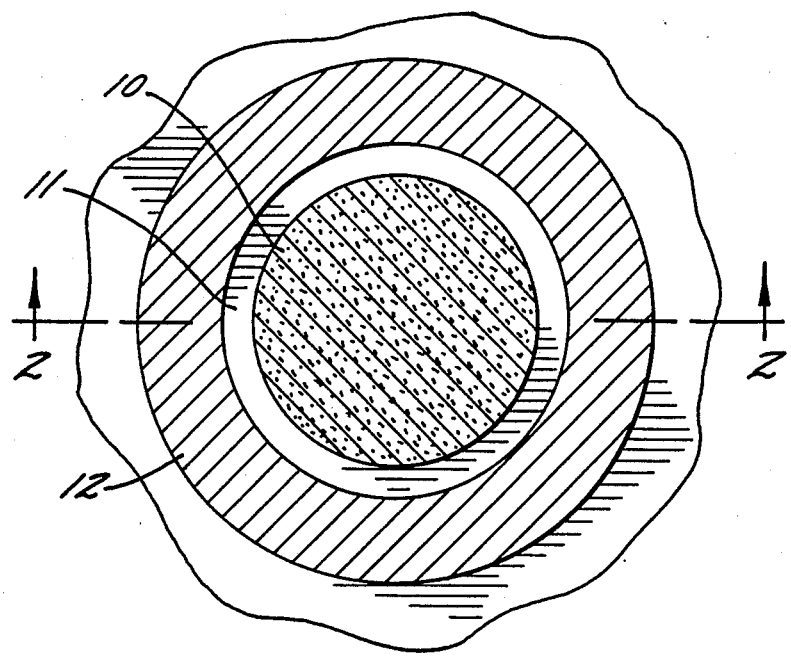
FIG. 1 is a top plan view of an MOS capacitor according to the present invention.

FIG. 1 is a top plan view of an MOS capacitor according to the present invention. In one preferred embodiment of the invention, the metal portion 10 is formed of polycrystalline silicon. As is know by those familiar with these materials, polycrystalline silicon is not a metal, but it is conductive when degenerately doped. Polycrystalline silicon is becoming more commonly used for this purpose, but the "metal" terminology used to describe MOS devices, including capacitors and transistors, has remained in use, and for the sake of clarity and consistency will be used herein.

As seen in FIG. 1, the design of one preferred embodiment of the invention is a series of concentric circles. Thus, the circular metal contact 10 is surrounded by the oxide portion 11 which in the illustrated embodiment is a layer of silicon dioxide. The oxide layer can be fashioned according to any appropriate technique; for example, thermal oxidation, chemical vapor deposition, or plasma enhanced chemical vapor deposition. Finally, an ohmic contact 12 forms a concentric circle around the oxide portion 11 and the metal contact 10 and in a particular embodiment is formed of tantalum silicide ($TaSi_2$), a novel material for this purpose.

Figure 2:
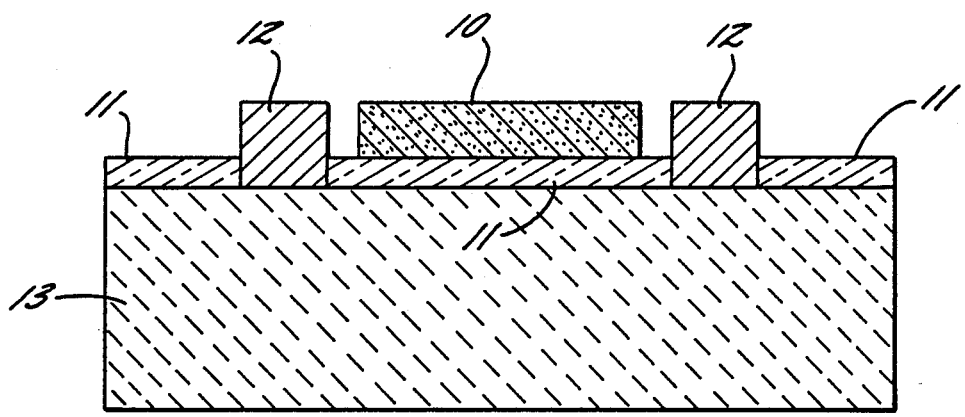
FIG. 2 is a cross-sectional view of the MOS capacitor taken along line 2—2 of FIG. 1.

In a cross-sectional view of FIG. 2, the same elements are visible, along with the silicon carbide portion 13, illustrating that in this embodiment of the invention, the ohmic contact and the active portion of the semiconductor are coplanar with one another upon the surface of the active region of the silicon carbide.

In other embodiments of the invention, the metal contact to the oxide can be selected to be specific to the desired function of the device. For example, for use in integrated circuits, the metal can be polysilicon as described above, aluminum, nickel or chromium, among others. For use as a gas sensor, a temperature sensor corrosion resistant metal such as chromium, nickel, platinum, palladium, silver or gold could be used.

Further to the invention, because the capacitance of the device will be related to both the area of metal-oxide contact and the thickness of the insulator, the diameter of the circular metal contact 10, and the insulator thickness can be selected to obtain a specific capacitance. The ohmic contact ring 12 is in close proximity to the oxide contact with only a very small gap, typically no more than 50 micrometers, separating them. The gap between the ohmic contact 12 and the metal contact 10, and the area outside of the ohmic contact 12, are passivated with the oxide 11, as illustrated in FIG. 2.

This particular design, which places a large area ohmic contact in very close proximity to the silicon carbide being depleted under the metal-oxide contact, greatly reduces the series resistance in the device, which in turn increases the capacitance range of the device. As stated earlier, series resistance is not typically a problem for MOS capacitors on silicon, however, silicon carbide is much more resistive. The device design of the present invention provides a method of reducing the series resistance which would otherwise be present in a silicon carbide device.

Additionally, the device design confines the device to the very top surface of the silicon carbide crystal. This allows the substrate to be of very resistant quality without a concurrent gain in series resistance. Tantalum silicide is used as the ohmic contact, as opposed to typical contacts formed of gold and tantalum alloys, or of nickel, because tantalum silicide is a superior ohmic contact and further aids in the reduction of series resistance.

EXAMPLE 1

Figure 3:
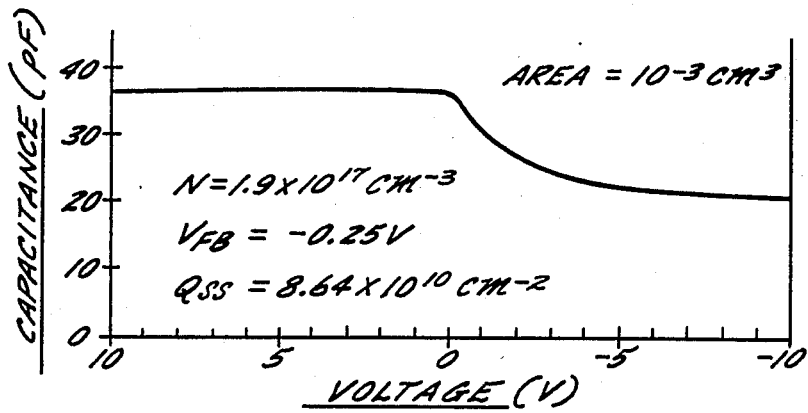
FIG. 3 is a plot of capacitance in picofarads against potential in volts for a capacitor according to the present invention using chromium as the metal in the metal-oxide contact.

FIG. 3 is a plot of capacitance in picofarads (pF) versus potential in volts for a metal-oxide-semiconductor capacitor according to the present invention. As stated in the description, the capacitor of FIG. 3 used chromium as the metal in the metal-oxide contact, which contact had an area of $1 \times 10^{-3}$ square centimeters ($cm^2$). The carrier concentration of this substrate was $1.9 \times 10^{17}$ $cm^{-3}$ and the capacitor demonstrated an excellent flatband voltage of $-0.25$ volts. The carrier concentration of a substrate was $1.9 \times 10^{17}$ $cm^{-3}$ and the fixed oxide charge was $8.64 \times 10^{10}$ $cm^{-2}$. The result was a flatband capacitance of 35.2 picofarads and a ratio of minimum capacitance to maximum capacitance ($C_{min}/C_{max}$) of 0.57.

EXAMPLE 2

Figure 4:
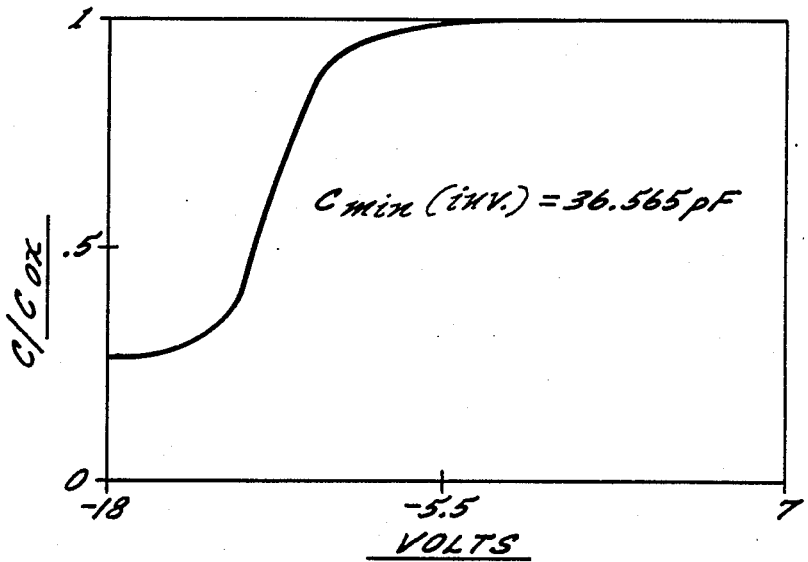
FIG. 4 is a similar plot for a capacitor according to the present invention using polycrystalline silicon as the metal in the metal-oxide contact.

FIG. 4 is a similar plot of the ratio of measured capacitance to the capacitance of the oxide versus potential for a capacitor according to the present invention which used polycrystalline silicon as the conductor in the metal-oxide contact. This particular capacitor had a metal contact area of approximately $2 \times 10^{-3}$ cm$^{-2}$, a carrier concentration of $1.72 \times 10^{16}$ cm$^{-3}$ and a fixed oxide charge of $4.28 \times 10^{12}$ cm$^{-2}$. The result was a capacitor which showed a flatband voltage of $-10.6$ volts, and a ratio of minimum capacitance to maximum capacitance of 0.264. Minimum capacitance was 36.6 pF and maximum capacitance was 138 pF.

EXAMPLE 3

Figure 5:
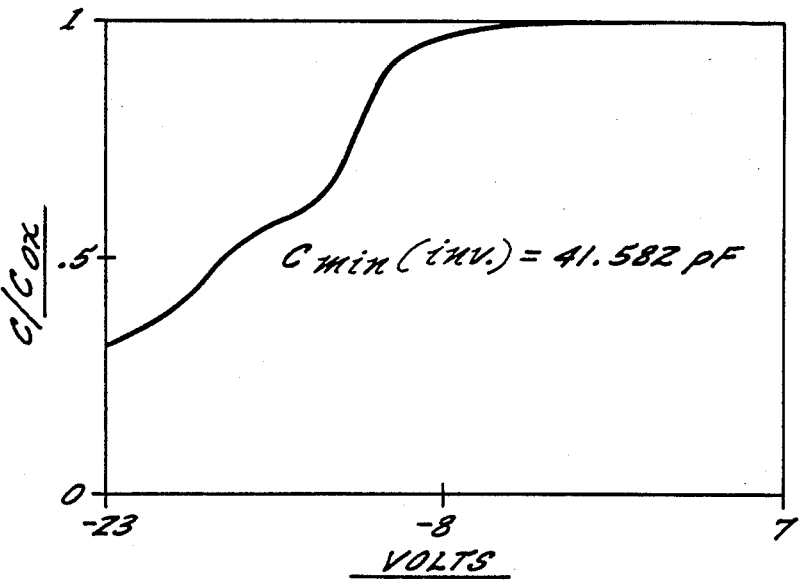
FIG. 5 is another plot for a capacitor according to the present invention using polycrystalline silicon as the metal, but with a different dopant density than the capacitor of FIG. 4.

FIG. 5 is another plot of the ratio of measured capacitance to the capacitance of the oxide versus voltage for another capacitance which used polycrystalline silicon as the metal, but with a different carrier density in the semiconductor than the capacitor of FIG. 4. This capacitor also had an area of approximately $2 \times 10^{-3}$ cm$^{-2}$, a carrier concentration of $2.61 \times 10^{16}$ cm$^{-3}$ and a fixed oxide charge of $4.42 \times 10^{12}$ cm$^{-2}$. This resulted in a capacitor which demonstrated a flatband voltage of $-11.2$ volts, and a ratio of minimum capacitance to maximum capacitance of 0.309. Minimum capacitance was 41.6 pF and maximum capacitance was 134 pF.

In the specification, there have been set forth preferred and exemplary embodiments of the invention which have been described by way of example, and not by way of limitation, the scope of the invention being set forth in the accompanying claims.

That which is claimed is:

1. A variable capacitance metal-insulator-semiconductor capacitor with reduced series resistance and lesser leakage current, suitable for operation at high temperatures and high radiation densities, and comprising:

a substantially variable capacitance doped semiconductor portion formed of silicon carbide having substantially uniform high resistivity for substantially varying the capacitance thereof when said doped semiconductor portion is depleted of carriers;

a substantially constant capacitance portion of insulator material upon one surface of said silicon carbide semiconductor portion;

a metal portion upon said substantially constant capacitance insulator portion for defining an active region of said silicon carbide semiconductor portion, and for variably depleting said active region of carriers when a bias is applied to said metal portion; and an ohmic contact upon said one surface of said silicon carbide semiconductor portion so that a bias applied to said metal portion variably depletes said silicon carbide semiconductor portion of carriers, substantially varies the capacitance of said silicon carbide semiconductor portion, and correspondingly substantially varies the total capacitance of said capacitor.

2. A capacitor according to claim 1 wherein said metal portion comprises a circular metal contact, and said ohmic contact comprises an annular contact surrounding the circumference of said circular metal contact with the inner circumference of said ohmic contact positioned within 50 micrometers or less of said circumference of said metal contact.

3. A capacitor according to claim 1 wherein said insulator material portion is selected from the group consisting of silicon dioxide and silicon nitride.

4. A capacitor according to claim 1 wherein said metal portion if selected from the group consisting of chromium, nickel, platinum, palladium, aluminum, silver, gold or polycrystalline silicon.

5. A capacitor according to claim 1 wherein said ohmic contact upon said doped semiconductor portion is positioned in direct contact with the insulator portion.

6. A capacitor according to claim 1 wherein said ohmic contact upon said doped semiconductor portion is positioned between within about 0.25 and about 250 microns of said active region of said semiconductor.

7. A capacitor according to claim 1 wherein said insulator material comprises thermally grown silicon dioxide.

8. A capacitor according to claim 1 wherein said insulator material comprises silicon dioxide deposited by chemical vapor deposition.

9. A capacitor according to claim 1 wherein said insulator material comprises a silicon dioxide layer deposited by plasma enhanced chemical vapor deposition.

10. A capacitor according to claim 1 wherein said ohmic contact upon said doped semiconductor portion and said insulator material are coplanar upon said active region of said semiconductor.

11. A capacitor according to claim 1 wherein said insulator material comprises silicon nitride.

12. A capacitor according to claim 11 wherein said silicon nitride comprises thermally grown silicon nitride.

13. A capacitor according to claim 11 wherein said silicon nitride comprises silicon nitride deposited by chemical vapor deposition.

14. A capacitor according to claim 11 wherein said silicon nitride comprises silicon nitride deposited by plasma enhanced chemical vapor deposition.

* * * * *

UNITED STATES PATENT AND TRADEMARK OFFICE
CERTIFICATE OF CORRECTION

PATENT NO. : 4,875,083
DATED : October 17, 1989
INVENTOR(S) : John W. Palmour

It is certified that error appears in the above-identified patent and that said Letters Patent is hereby corrected as shown below:

<u>Column 1,</u>
Line 3, the following statement should appear as the first paragraph:
-- The U.S. Government has a paid-up license in this invention and the right in limited circumstances to require the patent owner to license others on reasonable terms as provided for by the terms of contract N00014-82-K-0182 awarded by the Office of Naval Research. --

Signed and Sealed this

Fifteenth Day of March, 2005

JON W. DUDAS
*Director of the United States Patent and Trademark Office*